United States Patent
Gossens et al.

[11] Patent Number: 5,993,430
[45] Date of Patent: Nov. 30, 1999

[54] INTEGRALLY WRAPPED ABSORBENT ARTICLE AND METHOD OF WRAPPING

[75] Inventors: Anthonette A. Gossens; John P. Vukos, both of Neenah, Wis.

[73] Assignee: Kimberly-Clark Worldwide, Inc., Neenah, Wis.

[21] Appl. No.: 08/994,203

[22] Filed: Dec. 19, 1997

[51] Int. Cl.[6] .................................................. A61F 13/15
[52] U.S. Cl. .................. 604/385.1; 604/358; 604/385.2; 604/387
[58] Field of Search ................ 604/378, 385.2, 604/385.1; 521/63; 156/201

[56] References Cited

U.S. PATENT DOCUMENTS

| | | | |
|---|---|---|---|
| H1363 | 10/1994 | Leeker | 206/440 |
| H1454 | 6/1995 | Cucuzza et al. | 604/385.1 |
| 2,693,439 | 11/1954 | Blanchard et al. | |
| 2,834,459 | 5/1958 | Rickard et al. | 206/63.2 |
| 3,044,467 | 7/1962 | Campau | 128/290 |
| 3,062,371 | 11/1962 | Patience | 206/63.2 |
| 3,575,175 | 4/1971 | McGuire | 128/290 |
| 3,654,929 | 4/1972 | Nilsson et al. | 128/287 |
| 3,960,029 | 6/1976 | Brooks | 128/287 |
| 3,973,567 | 8/1976 | Srinivasan et al. | 128/290 R |
| 3,989,867 | 11/1976 | Sisson | 428/132 |
| 4,380,450 | 4/1983 | Reich | 604/386 |
| 4,402,689 | 9/1983 | Baum | 604/387 |
| 4,551,145 | 11/1985 | Ryan | 604/389 |
| 4,556,146 | 12/1985 | Swanson et al. | 206/440 |
| 4,564,108 | 1/1986 | Widlund et al. | 206/438 |
| 4,579,556 | 4/1986 | McFarland | 604/385 A |
| 4,608,047 | 8/1986 | Mattingly | 604/387 |
| 4,692,162 | 9/1987 | Binker et al. | 604/385 R |
| 4,735,316 | 4/1988 | Froidh et al. | 206/438 |
| 4,743,245 | 5/1988 | Lassen et al. | 604/385 R |
| 4,765,477 | 8/1988 | Froidh et al. | 206/438 |
| 4,773,905 | 9/1988 | Molee et al. | 604/378 |
| 4,781,712 | 11/1988 | Barbabino et al. | 604/385.1 |
| 4,802,884 | 2/1989 | Froidh et al. | 493/339 |

(List continued on next page.)

FOREIGN PATENT DOCUMENTS

| | | | |
|---|---|---|---|
| 0313426 | 4/1989 | European Pat. Off. | |
| 0350924 | 1/1990 | European Pat. Off. | A61F 13/15 |
| 0357000 | 3/1990 | European Pat. Off. | A61F 13/15 |
| 0472376 | 2/1992 | European Pat. Off. | |
| 0625345 | 11/1994 | European Pat. Off. | A61F 13/15 |
| 0699427 | 3/1996 | European Pat. Off. | A61F 13/15 |
| 4127411 | 10/1992 | Germany | |
| 2060398 | 5/1981 | United Kingdom | A61F 13/16 |
| 2221667 | 2/1990 | United Kingdom | |
| 2273279 | 6/1994 | United Kingdom | B65D 85/16 |
| 2277914 | 11/1994 | United Kingdom | B65D 85/16 |
| 8902728 | 4/1989 | WIPO | A61F 13/16 |
| 8902729 | 4/1989 | WIPO | A61F 13/18 |
| 9001311 | 2/1990 | WIPO | A61F 13/15 |
| 9207536 | 5/1992 | WIPO | A61F 13/56 |
| 9207537 | 5/1992 | WIPO | A61F 13/56 |

*Primary Examiner*—John G. Weiss
*Assistant Examiner*—Miley C. Peppers, III
*Attorney, Agent, or Firm*—Thomas J. Connelly; Thomas M. Parker; Douglas G. Glantz

[57] ABSTRACT

An intergrally wrapped sanitary protection absorbent article and method of wrapping are disclosed providing an absorbent configured to fit the pudendal region of a woman, and folded and enclosed in a liquid-impermeable baffle. In one aspect, the liquid-impermeable baffle has a first side on one side of the baffle width and a second side on the other side of the baffle width, opposite the first side, wherein the first side and the second side are sealed along their length to form side seals, such that the sides and the seals form the integrally wrapped sanitary protection absorbent article enclosure of the present invention. In one aspect, a first perforation strip on the first side seal and a second perforation strip on the second side seal make it convenient for opening the individually wrapped absorbent article package of the present invention.

19 Claims, 3 Drawing Sheets

U.S. PATENT DOCUMENTS

| | | | |
|---|---|---|---|
| 4,846,828 | 7/1989 | Mendelsohn | 604/387 |
| 4,857,066 | 8/1989 | Allison | 604/385.1 |
| 4,917,675 | 4/1990 | Taylor et al. | 604/385.1 |
| 5,413,568 | 5/1995 | Roach et al. . | |
| 5,478,336 | 12/1995 | Pigneul | 604/385.1 |
| 5,484,636 | 1/1996 | Berg, Jr. et al. . | |
| 5,569,228 | 10/1996 | Byrd et al. . | |
| 5,569,230 | 10/1996 | Fisher et al. . | |
| 5,611,879 | 3/1997 | Morman | 156/201 |
| 5,769,837 | 6/1998 | Parr . | |
| 5,810,798 | 9/1998 | Finch et al. | 604/378 |
| 5,824,004 | 10/1998 | Osborn, III et al. | 604/385.2 |
| 5,856,366 | 1/1999 | Shiveley et al. | 521/63 |

INTEGRALLY WRAPPED ABSORBENT ARTICLE AND METHOD OF WRAPPING

BACKGROUND OF THE INVENTION

1. Field of the Invention

This invention relates to an integrally wrapped sanitary protection absorbent article and method of wrapping designed to protect a user by absorbing or containing menstrual fluids and/or other body exudates. More specifically, this invention relates to an integrally wrapped sanitary protection absorbent article and method of wrapping which provide an integral pad wrapping around an individual feminine care sanitary pad.

2. Background of the Invention

Feminine sanitary protection devices designed to absorb body fluids, including menses, come in different functional designs. Sanitary napkins externally worn about the pudendal area are absorbent pads designed primarily for heavy menstrual flow. Panty liners or panty shields are thin sanitary napkin products worn about the pudendal area for light menstrual flow. Tampons are cylindrical absorbent pads positioned internally within the vagina.

Traditionally, sanitary napkins have been bundled with several napkins in each package. A single, large package is called on to keep all the napkins clean, sanitary, and undamaged. Unfortunately, however, when one napkin is removed from the package and carried individually in a pocket or purse, it becomes unprotected from dirt and deforming pressures.

In recent years, individually wrapped folded napkins have been provided with an outer wrap which can be removed by the user when the napkin is needed. Examples of individually wrapped sanitary napkins are found in Swanson et al., U.S. Pat. No. 4,556,146, and Froidh et al., U.S. Pat. Nos. 4,735,316 and 4,765,477. The method of wrapping protects the enclosed napkin from dirt and deformation until the wrapping is removed. Because the napkin is individually folded into a compact size, it becomes more convenient to carry. But, the individual wrapping of commercially available sanitary napkins typically increases manufacturing costs associated with the requisite materials and processing of these wraps. These additional production expenses can result ultimately in an increased cost of the product to the consumer.

Mattingly, U.S. Pat. No. 4,608,047, discloses a packaged, folded sanitary napkin having a central absorbent element having three segments folded over one onto another. An adhesive bearing flap is folded, and another flap is folded over to adhere to the adhesive bearing flap. The resulting folded napkin presents on its external surface essentially only the garment facing side of the napkin exposed.

Taylor, U.S. Pat. No. 4,917,675, discloses a sanitary napkin having a folded release strip in an individual napkin package.

SUMMARY OF THE INVENTION

Briefly, this invention relates to an integrally wrapped absorbent article including an absorbent having a first sheet surface and an opposite second sheet surface, the first sheet surface having a length and a width configured to fit the pudendal region of a woman. A liquid-impermeable baffle is secured to the first sheet surface, the baffle having a length and a width covering the first sheet surface, wherein the baffle width further extends beyond the width of the first sheet surface by less than about one inch. A garment-attachment adhesive is secured to the liquid-impermeable baffle to an inside surface of a crotch of an undergarment. An enclosure surrounds the absorbent, wherein the enclosure is formed from the liquid-impermeable baffle.

A method of wrapping the absorbent article includes the steps of providing an absorbent article having a liquid-permeable cover sheet, an absorbent, and a garment-attachment adhesive, the absorbent having a length and a width configured to fit the pudendal region of a woman, positioning a liquid-impermeable baffle between the absorbent and the garment-attachment adhesive, the baffle having a length and a width covering the absorbent, wherein the baffle width further extends laterally larger than the absorbent pad width by less than about one inch, and forming an enclosure surrounding the absorbent, wherein the enclosure is formed from the liquid-impermeable baffle.

The integrally wrapped absorbent article provides sanitary protection and includes a sanitary napkin, panty liner or panty shield having a folded absorbent pad of an unfolded length and a width configured to fit the pudendal region of a woman, a liquid-impermeable baffle having a length and a width covering the absorbent pad and further extending laterally beyond the absorbent pad width, and an enclosure surrounding the absorbent pad, wherein the enclosure is formed from the liquid-impermeable baffle.

In one aspect, the liquid-impermeable baffle has a first lateral side on one lateral side of the baffle width and a second lateral side on the opposite lateral side of the baffle width, opposite the first lateral side. The first lateral side is sealed along its length to form a first side seal, and the second lateral side is sealed along its length to form a second side seal, such that the first and the second lateral sides and the first and the second side seals form the enclosure of the integrally wrapped absorbent article of the present invention.

In another aspect, a first perforation strip on the first side seal and a second perforation strip on the second side seal make it convenient for opening the individually wrapped package of the present invention.

A feminine sanitary protection package is needed which provides an absorbent article having a sanitary napkin, panty liner or panty shield with individual wrapping without added manufacturing and material production costs.

A feminine sanitary protection package also is needed which provides for a less expensive absorbent article to be stored discreetly until use and which prevents soiling, contamination and deformation.

A general object of this invention is to provide an integrally wrapped absorbent article capable of absorbing and containing menstrual fluids and/or other body exudates.

It is an object of the present invention to provide an integrally wrapped absorbent article which facilitates cleanliness and discretion in packaging appearance.

A more specific object of this invention is to provide an integrally wrapped absorbent article which is individually wrapped.

Another object of the present invention is to provide an individually wrapped sanitary napkin or panty liner or shield having packaging and manufacturing cost advantages.

It is an object of the present invention to provide an individually wrapped sanitary napkin or panty liner or shield having cost of material advantages.

It is an object of the present invention to provide individually wrapped sanitary napkin or panty liner or shield having environmental impact advantages.

A further object of the present invention to provide individually wrapped sanitary napkin or panty liner or shield which uses less plastic material that is thrown away.

It is an object of the present invention to provide individually wrapped an integrally wrapped absorbent article which does not require a separate wrapper in order to be individually wrapped.

These and other objects and advantages of the present invention will become more apparent to those skilled in the art in view of the following detailed description and the accompanying drawings.

DETAILED DESCRIPTION OF THE PREFERRED EMBODIMENTS

An integrally wrapped sanitary protection absorbent article and method of wrapping the article are disclosed. The integrally wrapped absorbent article provides individual wrapping for protective, absorbent sanitary napkins and panty liners or shields for undergarments. The individually wrapped absorbent article provides for cleanliness and discretion in handling prior to use.

Figure 1:
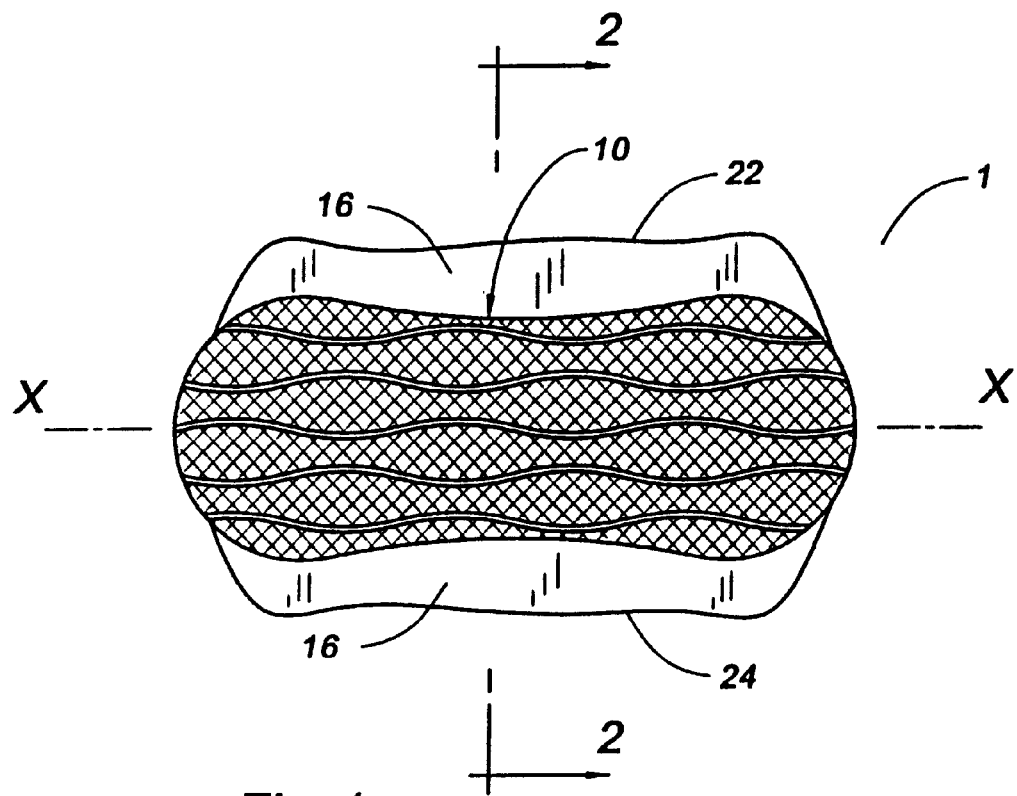
FIG. 1 is a top plan view of an initial configuration of the sanitary napkin or panty liner or shield of the present invention.
Figure 2:
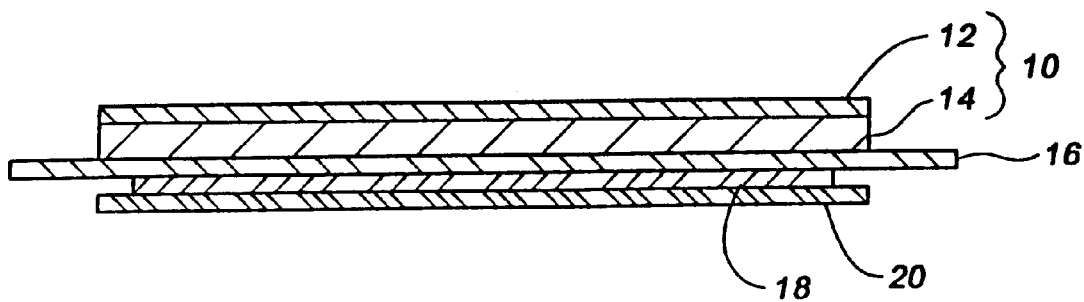
FIG. 2 is a cross sectional view, taken along line 2—2 of FIG. 1, of the initial configuration of the sanitary napkin or panty liner or shield of the present invention.

Referring now to FIGS. 1 and 2, an integrally wrapped absorbent article initial configuration 1 includes an absorbent pad 10 having an exterior profile in the shape of an hourglass.

The absorbent pad 10 includes a liquid-pervious cover 12 and an absorbent 14.

A liquid-impermeable baffle 16 of the integrally wrapped absorbent article initial configuration 1 is designed to permit the passage of air or vapor out of the absorbent pad 10 while blocking the passage of body fluid.

Such sanitary napkin and panty liner or shield pads 10 are designed for adhesive attachment to the inside surface of the crotch portion of an undergarment. The absorbent articles 10 are constructed from layers of a liquid-permeable cover 12 and an absorbent 14, vertically arranged.

The liquid-impermeable baffle 16 is constructed and utilized as the individual absorbent pad wrapper. The liquid-impermeable baffle 16 can provide the individual absorbent pad wrapper because of an extra poly film width located along both a first side 22 and a second side 24 of the baffle 16. The first side 22 is situated on one side of the baffle 16 width as viewed relative to the longitudinal axis X—X, and the second side 24 is situated on the other side of the width of the baffle 16, opposite to the first side 22.

The first side 22 and second side 24 of the baffle 16 have a dimension which extends beyond the width of absorbent pad 10. Even though the larger width of baffle 16 will be used to enclose the absorbent pad 10, the dimension of first side 22 and second side 24 of the baffle 16 which extends beyond the width of absorbent pad 10, however, is not required to be sufficient to fold completely over the absorbent pad 10. The larger width of baffle 16 need only be on the order of less than one inch on each side, for example, which extends beyond the width of absorbent pad 10.

A garment attachment adhesive 18 is secured to a lower surface of the baffle 16, and the adhesive 18 can be covered by a removable release strip 20.

Figure 3:
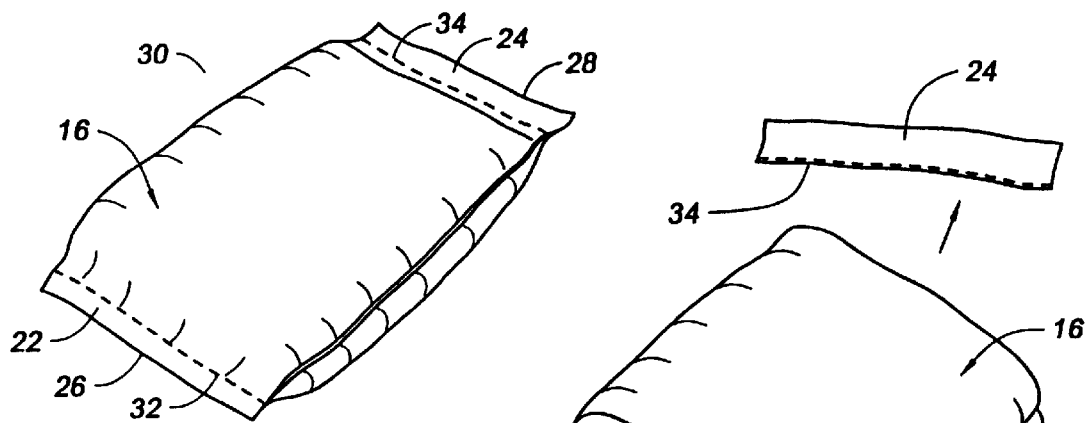
FIG. 3 shows a perspective view of an integrally wrapped absorbent article of the present invention and how it is deployed for use.

Referring now to FIGS. 3–6, the individually wrapped absorbent article 30 of the present invention is shown as it is folded, enclosed, and sealed, and then how it is opened, unfolded, and deployed for use. Referring to FIG. 3, the individually wrapped absorbent article 30 of the present invention is folded in such a way that the extra width of the poly baffle 16 can be folded and 22 and 24 bonded together, effecting the seals 22 and 24 for a wrapped appearance. The liquid-impermeable baffle enclosure 16 encloses the absorbent pad wherein the first side 22 is sealed along its length to form a first side seal 26, and the second side 24 is sealed along its length to form a second side seal 28. The first side 22 and the first side seal 26 and the second side 24 and the second side seal 28 form the baffle enclosure 16 of the individually wrapped absorbent pad 30.

Figure 4:
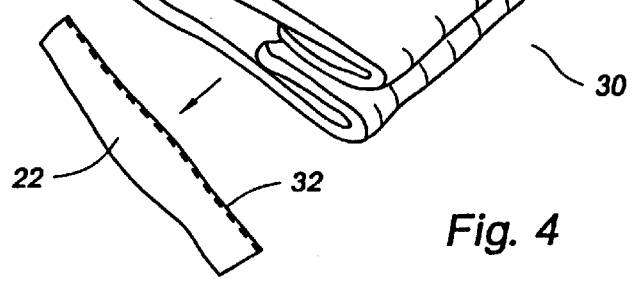
FIG. 4 shows a perspective view of the integrally wrapped absorbent article of the present invention and how the wrapping is opened.

A perforation 32 is formed on the first side 22, and a perforation 34 is formed on the second side 24 as shown in FIG. 3. These perforations 32 and 34 allow the extra material of the baffle 16 poly to be torn away to unwrap the absorbent article 30 as shown in FIG. 4. When both of the perforated sides, 32 and 34, respectively, have been torn away as shown in FIG. 4, the absorbent article 40 can be unfolded as shown in FIGS. 5 and 6 and used as a normal pad.

Figure 5:
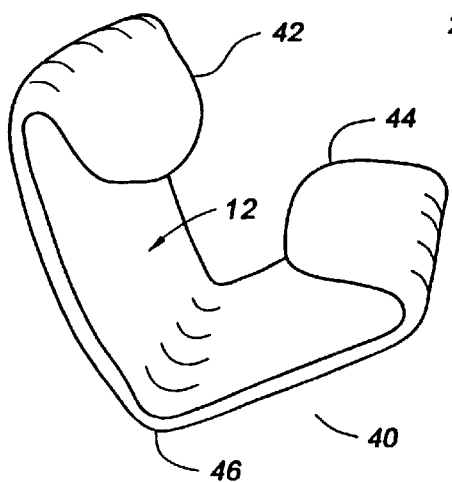
FIG. 5 shows a perspective view of the integrally wrapped absorbent article of the present invention and how the folded article is opened.

Referring now to FIG. 5, absorbent article 40 has the extra material of the baffle 16 poly removed. Absorbent article 40 is shown folded in the following manner. A first end 42 and an opposite second end 44 are folded inward toward the liquid-permeable cover 12. Each of the ends 42 and 44 is folded a distance approximately equal to one-sixth of the total length of the absorbent article 40. The absorbent article 40 is then folded approximately at the middle 46 of the overall length of absorbent article 40, leaving only the garment-facing side of the absorbent article 40 visible. This method of folding is preferred because the entire body-facing surface of the absorbent article 40 is protected from contamination.

Figure 6:
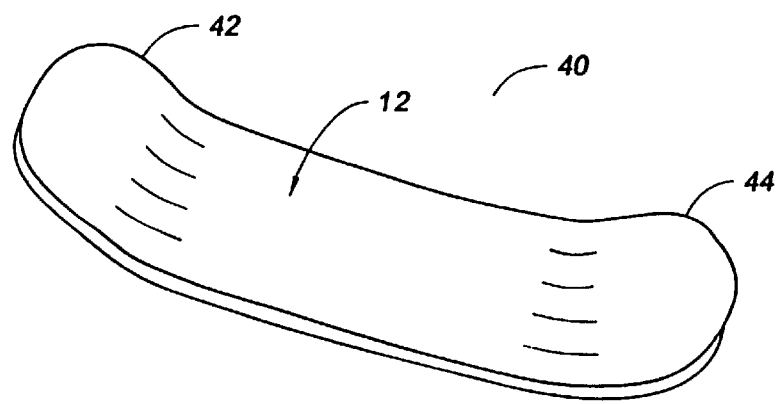
FIG. 6 shows a perspective view of the integrally wrapped absorbent article of the present invention and how the article is unfolded.

Referring to FIG. 6, the absorbent article 40 is shown unfolded and deployed for use.

Figure 7:
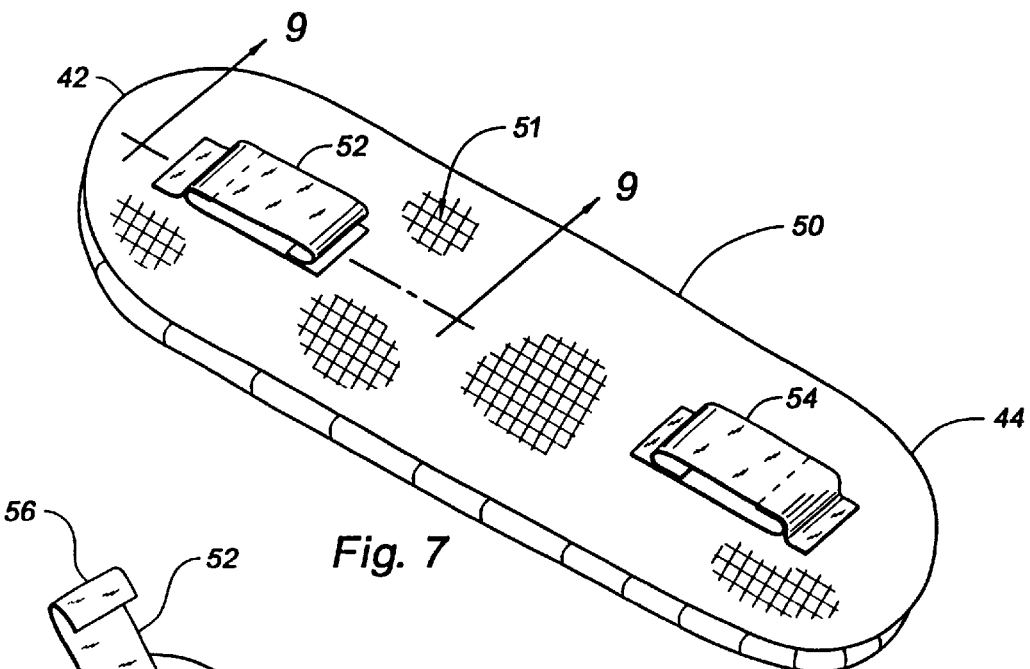
FIG. 7 shows a perspective view of an integrally wrapped absorbent article of the present invention having garment attachment tape.
Figure 8:
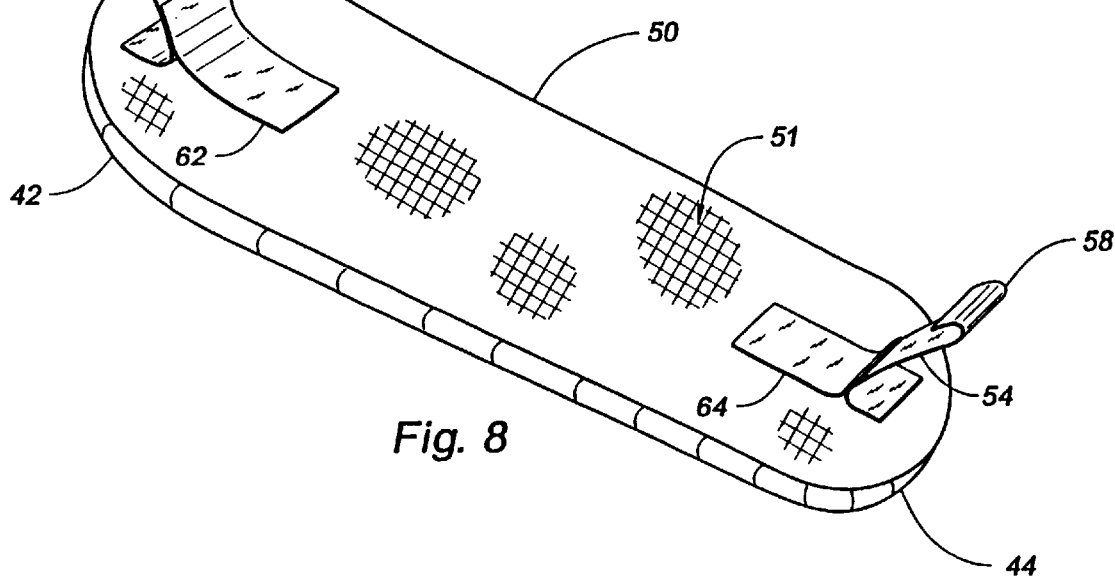
FIG. 8 shows a perspective view of the integrally wrapped absorbent article of the present invention and showing how the attachment tape is opened.
Figure 9:
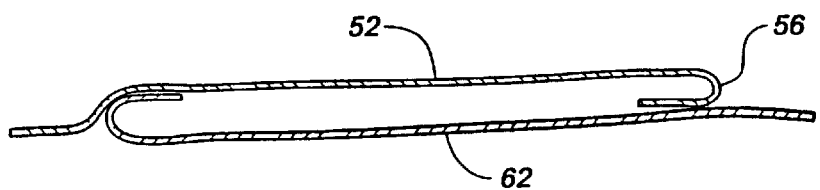
FIG. 9 shows an elevation view of a garment attachment tape as used on the absorbent article of the present invention.

Referring now to FIGS. 7, 8, and 9, individually wrapped sanitary absorbent pad 50 is shown unfolded and ready for use. The absorbent pad 50 has a first end 42, an opposite second end 44, and a garment-facing liquid-impermeable baffle 51 opposite the liquid-permeable cover or top sheet 12. The absorbent article 50 is shown having an extra material of the baffle 51 poly removed in accordance with the individually wrapped absorbent article 50 of the present invention shown in an unwrapped condition.

A garment attachment tape 52 and a garment attachment tape 54 are provided for attachment of the absorbent article 50 to the inside surface of the crotch of an undergarment. The garment attachment tape 52 and the garment attachment tape 54 are spaced apart and aligned opposite to the liquid-permeable body side cover 12.

Referring now to FIG. 8, a finger tab 56 and a finger tab 58 are provided for pulling the garment attachment tapes 52 and 54 from a release tape 62 and a release tape 64 by pulling the finger tab 56 and the finger tab 58, respectively. In use, the woman pulls pack the attachment tapes 52 and 54 on each end 42 and 44 with the finger tabs 56 and 58.

Referring now to FIG. 9, the attachment tapes 52 and 54 having the finger tabs 56 and 58 are shown adjacent the release tapes 62 and 64.

The alternate means of garment attachment having attachment is tape as shown in FIGS. 7, 8, and 9 provides advantages of not having to dispose of the conventional peel strip.

The absorbent pad 10, 40, or 50 can be formed in the shape of a race track or oval or the like. The absorbent pad 10, 40, or 50 can have other shapes, e.g., such as rectangular shapes other than oval or race track shape, provided that the shapes are designed to cover the pudendal region of a woman. The absorbent pad 10, 40, or 50 can be viewed as having a central longitudinal axis X—X. Most absorbent pad articles 10, 40, or 50, such as sanitary napkins and panty liners or shields, are layered in sheets which are longer than they are wide. In addition to the absorbent 14 and the liquid-permeable cover 12, other layers also can be utilized, such as a transfer layer, a layer of anhydrous deodorant material, a layer containing super-absorbent materials, and additional absorbent layers.

The various layers can be vertically stacked, assembled, laminated, and/or bonded together to form the sheet or web of material from which the articles 10, 40, or 50 are later cut or stamped out, prior to attachment of baffle 16 or 51. The various layers can be bonded together by using heat, pressure, heat and pressure, adhesive, hot melt glue, stitching with thread, ultrasonic bonding, mechanical bonding, thermal bonding, chemical bonding, or a combination of these and/or other means known to those skilled in the art.

The liquid-impermeable baffle 16 or 51 is designed to permit the passage of air or vapor out of the absorbent articles 10, 40, or 50 while blocking the passage of body fluid. The liquid-impermeable baffle 16 can be made from any material having these properties. The baffle 16 also can be constructed from a material that will block the passage of vapor as well as fluids, if desired. A good material from which the liquid-impermeable baffle 16 or 51 can be constructed is a micro-embossed, polymeric film, such as polyethylene or polypropylene. Bi-component films can also be used. A preferred material is polyethylene film. Most preferably, the polyethylene film will have a thickness in the range of from about 0.5 mil to about 2.0 mil.

Construction adhesive can be used in articles 10, 40, or 50 to attach and bond the various layers together. For example, referring to FIG. 2, construction adhesive can be used to bond the liquid-impermeable baffle 16 to the absorbent 14 or to bond the absorbent 14 to the liquid-permeable cover 12. The presence of such construction adhesive and the amount used will depend upon manufacturing specifications. Useful construction adhesives are commercially sold by National Starch and Chemical Company, having an office located at 10 Finderne Ave., Bridgewater, N. J. 08807.

The liquid-permeable cover 12 is designed to contact the body of the wearer and can be constructed of a woven or non-woven material which is easily penetrated by body fluid. The liquid-permeable cover 12 also can be formed from either natural or synthetic fibers. Suitable materials include bonded carded webs of polyester, polypropylene, polyethylene, nylon, or other heat-bondable fibers. Other polyolefins, such as copolymers of polypropylene and polyethylene, linear low-density polyethylene, finely-perforated film webs and net materials, also work well. A preferred material is a composite of an apertured thermoplastic film positioned above a non-woven fabric material. Such a composite material can be formed by extrusion of a polymer onto a web of spunbond material to form an integral sheet. One example of this material is an apertured, thermoplastic polyethylene film bonded to a spunbond material. Spunbond material is a non-woven material which is manufactured and commercially sold by Kimberly-Clark Corporation having an office located at 401 N. Lake Street, Neenah, Wis. 54956. The apertured film/non-woven laminate exhibits a smooth appearance and is soft to the touch. This material is soft and does not irritate the wearer's skin and yet has a cushioned feel because of its bulk. Another material useful as the liquid-permeable cover 12 is a spunbond web of polypropylene. This spunbond web can contain from between about 1 percent to about 6 percent of a whitening agent, such as titanium dioxide ($TiO_2$) or calcium carbonate ($CaCO_3$) to give it a clean, white appearance. A uniform thickness of spunbond is desirable because it will have sufficient strength, after being perforated, to resist being torn or pulled apart during use. The most preferred polypropylene webs have a basis weight of between about 18 grams per square meter ($g/m^2$) to about 40 $g/m^2$. An optimum weight is between about 30 $g/m^2$ to about 40 $g/m^2$.

The absorbent layer 14 can be present as a single layer or as two or more distinct layers. The absorbent layer 14 can be formed from various natural or synthetic fibers such as wood pulp fibers, virgin cellulose fibers, regenerated cellulose fibers, cotton fibers, peat moss, or a blend of pulp and other fibers. The absorbent layer 14 also could be formed from a fine pore fabric such as wet-laid, air-dried tissue or from an uncreped through air-dried (UCTAD) tissue having a basis weight of from about 30 $g/m^2$ to about 120 $g/m^2$. The UCTAD tissue can be prepared by a process disclosed in U.S. Pat. No. 5,048,589 issued to Crook et al. on Sep. 17, 1991. The UCTAD tissue is disclosed in U.S. Pat. No. 5,399,412 issued to Sudall et al. on Mar. 21, 1995. Each of these patents is incorporated by reference and made a part hereof. The absorbent layer 14 also may be comprised of other well-known materials such as cellulose fibers, rayon fibers, cellulose sponge, hydrophilic synthetic sponge, for example polyurethane, and the like.

The absorbent articles 10 also include one or more elongated strips or areas of a garment attachment adhesive 18, for example, referring to FIG. 2, secured to the bottom surface of the liquid-permeable baffle 16. The garment attachment adhesive 18 functions to attach the absorbent articles 10 to the inner crotch portion of an undergarment during use. The garment attachment adhesive 18 enables the sanitary napkin or panty liner to be properly aligned and retained relative to the user's vaginal opening so that maximum fluid protection can be obtained. The garment attachment adhesive 18 can cover a portion of the bottom surface of the liquid-impermeable baffle 16. The garment attachment adhesive 18 can consist of a swirl pattern of adhesive or be one or more strips of adhesive or various other patterns. The garment attachment adhesive 18 also can consist of a plurality of adhesive dots which are randomly or uniformly arranged on the exterior surface of the baffle 16. When in strip form, e.g., by way of example, in a single wide strip, the garment attachment adhesive 18 can be aligned along the central longitudinal axis X—X of the absorbent articles 10, respectively. Alternatively, the garment attachment adhesive 18 can be present as two or more spaced apart longitudinal strips. The garment attachment adhesive 18 is of such a nature that it will allow the user to remove the absorbent article 10 and reposition it on her undergarment if needed. A hot melt adhesive which works well as the garment attachment adhesive is commercially sold by National Starch and Chemical Company having an office located at 10 Finderne Avenue, Bridgewater, N.J. 08807.

In order to protect the garment attachment adhesive 18 from contamination or drying prior to use, the adhesive 18 can be protected by a releasable peel strip 20, for example, referring to FIG. 2. The release strip 20 can be a white Kraft paper which is coated on one side so that it can be released from the adhesive 18. The coating can be a silicone coating, such as a silicone polymer commercially available from Akrosil having an office located at 206 Garfield Avenue, Menasha, Wis. 54952. The release strips 20 are designed to be removed by the user prior to attachment of the absorbent articles 10, respectively, to the inner crotch portion of her undergarment.

The integrally wrapped sanitary protection absorbent article and method of wrapping of the present invention do not require a separate wrapper or releasable peel strip in order to be individually wrapped. The integrally wrapped sanitary protection absorbent article and method of wrapping provides advantages in both the cost of materials and in environmental impact. Although less plastic that is thrown away, still providing the cleanliness of individual wrapping is provided.

Now, an integrally wrapped absorbent article and method of wrapping have been developed which provide a sanitary napkin or panty liner with individual wrapping without added manufacturing and material production costs. The integrally wrapped absorbent article of the present invention provides a less expensive absorbent article which is individually wrapped, having packaging cost advantages, having cost of material advantages, and having environmental impact advantages. The integrally wrapped feminine sanitary protection packaging of the present invention provides a less expensive napkin to be stored discreetly until use and which prevents soiling contamination and deformation. The integrally wrapped sanitary protection package fills a woman's need to have an inexpensive absorbent article readily accessible and which facilitates cleanliness and discretion in packaging appearance.

While the invention has been described in conjunction with several embodiments, it is to be understood that many alternatives, modifications, and variations will be apparent to those skilled in the art in light of the foregoing description. Accordingly, this invention is intended to embrace all such alternatives, modifications, and variations which fall within the spirit and scope of the appended claims.

We claim:

1. An integrally wrapped sanitary protection absorbent article, comprising:

(a) an absorbent having a first sheet surface and an opposite second sheet surface, said first sheet surface having a length and a width configured to fit the pudendal region of a woman;

(b) a liquid-impermeable baffle secured to said first sheet surface, said baffle having a length and a width covering said first sheet surface, wherein said baffle width further extends beyond the width of said first sheet surface by less than about one inch;

(c) a garment-attachment adhesive for securing said liquid-impermeable baffle to an inside surface of a crotch of an undergarment;

(d) an enclosure surrounding said absorbent, wherein said enclosure is formed from said liquid-impermeable baffle; and (e) wherein said liquid-impermeable baffle has a first lateral side on one side of said baffle width and a second lateral side on the other side of said baffle width, opposite said first lateral side, and wherein said first lateral side is sealed along its length to form a first side seal and said second lateral side is sealed along its length to form a second side seal, wherein said first lateral side and said first side seal and said second lateral side and said second side seal form said enclosure.

2. The integrally wrapped sanitary protection absorbent article of claim 1 further comprising a perforation on said enclosure.

3. The integrally wrapped sanitary protection absorbent article of claim 2 comprising a first perforation strip on said first side seal and a second perforation strip on said second side seal.

4. The integrally wrapped sanitary protection absorbent article of claim 3 wherein said absorbent is folded within said enclosure.

5. The integrally wrapped sanitary protection absorbent article of claim 4 wherein said absorbent further comprises a liquid-permeable cover sheet covering said second sheet surface on a sheet side opposite said garment-attachment adhesive.

6. The integrally wrapped sanitary protection absorbent article of claim 5 wherein said absorbent has a first longitudinally oriented end, an opposite second longitudinally oriented end, and a garment-facing sheet side opposite said liquid-permeable cover sheet, said first and second ends being folded inward toward said liquid-permeable cover sheet a distance of about one-sixth of said absorbent length, said absorbent then being further folded in a middle of said absorbent length, such that only said garment-facing sheet side of said absorbent is exposed.

7. The integrally wrapped sanitary protection absorbent article of claim 5 wherein said absorbent article further comprises at least one garment-attachment tape having a finger tab, wherein said garment-attachment tape is positioned to be pulled from a release tape fixed to said liquid-impermeable baffle.

8. The integrally wrapped sanitary protection absorbent article of claim 5 wherein said absorbent comprises an absorbent pad selected from the group consisting of a sanitary napkin and a panty liner.

9. A method of wrapping an integrally wrapped sanitary protection absorbent article comprising the steps of:

(a) providing an absorbent article having a liquid permeable cover sheet, an absorbent, and a garment-attachment adhesive, said absorbent having a length and a width configured to fit the pudendal region of a woman;

(b) positioning a liquid-impermeable baffle between said absorbent and said garment-attachment adhesive, said baffle having a length and a width covering said absorbent, wherein said baffle width further extends laterally larger than said absorbent pad width by less than about one inch; and (c) forming an enclosure surrounding said absorbent, wherein said enclosure is formed from said liquid-impermeable baffle and provides a completely sealed enclosure for protecting said absorbent from contamination.

10. The method for wrapping an integrally wrapped sanitary protection absorbent article as set forth in claim 9 wherein said positioning a liquid-impermeable baffle comprises providing a liquid-impermeable baffle having a first lateral side on one lateral side of said baffle width and a second lateral side on the opposite lateral side of said baffle width, and wherein said first lateral side is sealed along its length to form a first side seal and said second lateral side is sealed along its length to form a second side seal, wherein said first lateral side and said first side seal and said second lateral side and said second side seal are attached to form said enclosure.

11. The method of wrapping an integrally wrapped sanitary protection absorbent article as set forth in claim 9 further comprising providing a perforation on said enclosure.

12. The method of wrapping an integrally wrapped sanitary protection absorbent article as set forth in claim 11 comprising providing a first perforation strip on said first side seal and a second perforation strip on said second side seal.

13. The method of wrapping an integrally wrapped sanitary protection absorbent article as set forth in claim 12 wherein said absorbent has a first longitudinal end, an oppositely aligned second longitudinal end, a liquid sheet, and a garment-facing sheet side aligned opposite to said liquid permeable cover sheet, and further comprising folding said first and second longitudinal ends inward toward said liquid pervious top sheet a distance of about one-sixth of the length of said absorbent, and folding said absorbent in a middle section of the length of said absorbent such that only said garment-facing cover sheet of said absorbent is exposed.

14. The method of wrapping an integrally wrapped sanitary protection absorbent article as set forth in claim 9 further comprising providing at least one garment-attachment tape having a finger tab, and positioning said finger tab to pull said garment-attachment tape from a release tape fixed to said garment-facing cover sheet.

15. An integrally wrapped sanitary protection absorbent article comprising:

(a) a folded absorbent having a liquid-pervious cover sheet, an absorbent, and a garment-attachment adhesive positioned on a sheet side of said absorbent pad opposite said liquid-permeable cover sheet, said absorbent having an unfolded length and a width configured to fit the pudendal region of a woman;

(b) a liquid-impermeable baffle positioned between said absorbent and said garment-attachment adhesive, said baffle having a length and a width covering said absorbent pad, wherein said baffle width further extends laterally larger than said absorbent pad width by less than about one inch;

(c) an enclosure surrounding said absorbent, wherein said enclosure is formed from said liquid-impermeable baffle, wherein said liquid-impermeable baffle has a first lateral side on one side of said baffle width and a second lateral side on the other side of said baffle width, opposite said first lateral side, and wherein said first lateral side is sealed along its length to form a first side seal and said second lateral side is sealed along its length to form a second side seal, wherein said first lateral side and said first side seal and said second lateral side and said second side seal form said enclosure; and (d) a first perforation strip on said first side seal and a second perforation strip on said second side seal.

16. The integrally wrapped sanitary protection absorbent article of claim 15 wherein said liquid-impermeable baffle is composed of a material which permits the passage of air or vapor out of said absorbent.

17. The integrally wrapped sanitary protection absorbent article of claim 16 wherein said liquid-impermeable baffle is composed of a material of micro-embossed polymeric film.

18. The integrally wrapped sanitary protection absorbent article of claim 17 wherein said micro-embossed polymeric film comprises polyethylene film.

19. The integrally wrapped sanitary protection absorbent article of claim 16 wherein said micro-embossed polymeric film comprises polypropylene film.

* * * * *

UNITED STATES PATENT AND TRADEMARK OFFICE
CERTIFICATE OF CORRECTION

PATENT NO.    : 5,993,430
DATED         : November 30, 1999
INVENTOR(S)   : Anthonette Gossens It is certified that error appears in the above-identified patent and that said Letters Patent is hereby corrected as shown below:

Column 1,
Lines 36, 46 and 54, change "U.S. Pat." to -- U.S. Patent --.

Column 3,
Lines 15, 18, 19, 21 and 24, change "FIG." to -- FIGURE --.
Lines 27, 30, 33 and 36, change "FIG." to -- FIGURE --.
Line 39, change "FIG." to -- FIGURE --.
Line 52, change "FIGS." to -- FIGURES --.

Column 4,
Line 24, change "FIGS." to -- FIGURES --.
Lines 27, 41 and 43, change "FIG." to -- FIGURE --.
Lines 45, 47 and 60, change "FIG." to -- FIGURE --.
Lines 46 and 62, change "FIGS." to -- FIGURES --.

Column 5,
Lines 10, 16 and 62, change "FIG." to -- FIGURE --.
Line 21, change "FIGS." to -- FIGURES --.

Column 6,
Line 2, change "N.J." to -- New Jersey --.
Line 22, change "Wis." to -- Wisconsin --.
Line 47, change "Pat." to -- Patent --.
Line 47, change "Sep." to -- September --.
Line 48, change "Pat." to -- Patent --.
Line 49, change "Mar." to -- March --.
Line 57, change "FIG." to -- FIGURE --.

UNITED STATES PATENT AND TRADEMARK OFFICE
CERTIFICATE OF CORRECTION

PATENT NO.   : 5,993,430
DATED        : November 30, 1999
INVENTOR(S)  : Anthonette Gossens It is certified that error appears in the above-identified patent and that said Letters Patent is hereby corrected as shown below:

Column 7,
Line 15, change "N.J." to -- New Jersey --.
Line 20, change "FIG" to -- FIGURE --.
Line 25, change "Wis." to -- Wisconsin --.

Column 8,
Line 31, change "3" to -- 2 --.

Signed and Sealed this

Twenty-ninth Day of April, 2003

JAMES E. ROGAN
*Director of the United States Patent and Trademark Office*